United States Patent [19]

Dellacoletta

[11] Patent Number: 5,208,346
[45] Date of Patent: May 4, 1993

[54] SIMPLIFIED PROCESS FOR THE PREPARATION OF AROMATIC BISMIDES

[75] Inventor: Brent A. Dellacoletta, Evansville, Ind.

[73] Assignee: General Electric Company, Pittsfield, Mass.

[21] Appl. No.: 851,667

[22] Filed: Mar. 16, 1992

[51] Int. Cl.$^5$ .......................................... C07D 209/02
[52] U.S. Cl. ...................................................... 548/461
[58] Field of Search .......................................... 548/451

[56] References Cited

U.S. PATENT DOCUMENTS 3,992,406 11/1976 Markezich ............................ 548/461
4,017,511 4/1977 Williams, III ........................ 548/461

OTHER PUBLICATIONS

CA 114: 123305h Aromatic . . . preparation, Dahl et al., 1991.
CA 114: 7811w Curable imide . . . compositions, Stenzenberger et al. p. 41, 1991.

Primary Examiner—Mary C. Lee
Assistant Examiner—Joseph K. McKane

[57] ABSTRACT

Method of preparing aromatic bisimides by effecting a reaction between a 3-substituted N-arylphthalimide and an aromatic dihydroxy dianion compound by refluxing in a non-polar organic solvent. Advantageously, the method eliminates the need for using a phase transfer catalyst or a dipolar aprotic solvent.

10 Claims, No Drawings

SIMPLIFIED PROCESS FOR THE PREPARATION OF AROMATIC BISMIDES

BACKGROUND OF THE INVENTION

This invention is directed to a novel method for preparing an aromatic bisimide by a process of effecting a reaction between a 3-substituted N-arylphthalimide and an aromatic dihydroxide dianion. More specifically, this invention relates to a simplified method for preparing an aromatic bisimide by effecting a reaction between a 3-substituted N-arylphthalimide and an aromatic dihydroxide dianion in a non-polar solvent without the use of a phase transfer catalyst.

Aromatic bisimides are valuable precursors for the synthesis of polyetherimides (See for example, U.S. Pat. Nos. 4,011,198 and 3,905,942, both issued to Takekoshi et al. in 1977 and 1975, respectively). Polyetherimides have a wide variety of uses such as in automobile parts, airplane parts, insulation for wires and various components for electrical appliances and the like. Polyetherimides also can be blended with other thermoplastic elastomeric resins to improve their physical properties, such as flame retardance, blow moldability and resistance to crack.

It is well known that the reaction of N-alkylnitrophthalimides, such as 4-nitro-N-methylphthalimide (4-NPI), with phenoxide salts, such as the disodium salt of bisphenyl-A (BPA), requires the use of a phase transfer catalyst, such as tetrabutyl ammonium bromide and/or a dipolar aprotic solvent, such as dimethyl sulfoxide (DMSO) or N,N-dimethylformamide (DMF). In fact, in the absence of either a dipolar aprotic solvent or a phase transfer catalyst, the reaction between the disodium salt of BPA and 4-NPI in a non-polar solvent, such as toluene, does not occur even after several hours of refluxing.

U.S. Pat. No. 3,992,406, issued to Markezich in 1976, for example, describes a method for preparing aromatic bisimides by effecting a reaction between a 3- or 4-nitro-N-substituted phthalimide with an aromatic dihydroxy compound in a dipolar aprotic solvent. The dipolar aprotic solvent is selected from the class consisting of dimethyl sulfoxide, N,N-dimethyl acetamide, N,N-dimethyl formamide (DMF), N-methyl pyrrolidone and mixtures thereof. Markezich's reaction is also carried out in the presence of an alkali-metal fluoride such as a fluoride selected from the class consisting of potassium, cesium and rubidium fluorides.

U.S. Pat. No. 4,017,511, issued to Williams, III in 1977, also describes the preparation of aromatic bisimides by reacting a 3- or 4-nitro-N-substituted phthalimide with an aromatic dihydroxy compound. Williams's reaction is carried out in the presence of an alkali-metal hydroxide and a dipolar aprotic solvent, e.g., dimethyl formamide.

The above current methods however incur costs. Dipolar aprotic solvents are expensive, very difficult to recover and purify and are moderately toxic. Phase transfer catalysts are also expensive and difficult to recover, and in addition partially decompose during a reaction, thereby affording nitrosamines which are known carcinogens. Consequently, there is a need for a more economic and safer method for preparing aromatic bisimides.

Surprisingly, it has now been discovered that aromatic bisimides can be produced without the use of the phase transfer catalyst or dipolar aprotic solvent. Specifically, 3-substituted N-arylphthalimides can be reacted with an aromatic dihydroxide to give excellent yields of an aromatic bisimide by refluxing in a non-polar solvent. Consequently, the present process is less expensive and eliminates the hazards found in prior methods.

SUMMARY OF THE INVENTION

The present invention relates to a process for preparing aromatic bisimides by effecting a reaction between a 3-substituted N-arylphthalimide and an alkali salt of an aromatic dihydroxy compound in a non-polar solvent and without the use of a phase transfer catalyst.

DETAILED DESCRIPTION OF THE INVENTION

The present invention relates to a simplified process for preparing aromatic bisimides such as those bisimides having the general formula

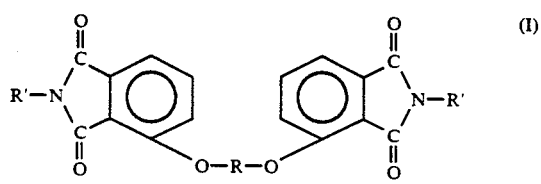

The process for example comprises effecting a reaction between a 3-substituted N-arylphthalimide of the general formula

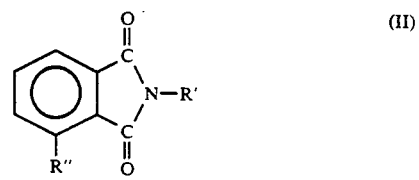

with the dianion of an aromatic dihydroxy compound of the general formula

where Z is an alkali metal such as Na, K, etc., R comprises (a) divalent radicals of the formula

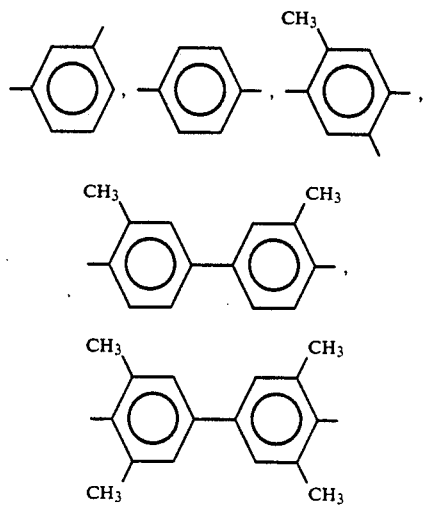

-continued

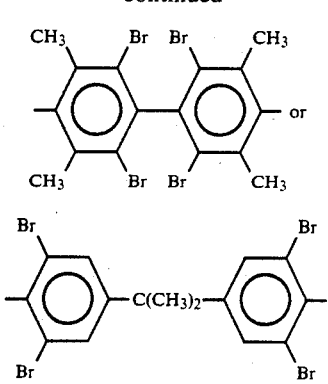

or (b) divalent organic radicals of the general formula

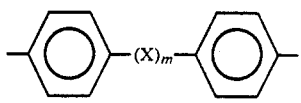

where X comprises a divalent radical of the formula $-C_yH_{2y}-$, $-CO-$, $-SO_2-$, $-SO-$, $-O-$ or $-S-$ where m is 0 or 1 and y is a whole number from 1 to 5. R' is a monovalent aryl radical of from 6 to 20 carbon atoms, and R'' comprises $-NO_2$, CN, F, Br, or Cl.

Suitable 3-substituted N-arylphthalimides of formula II include, for example, 3-nitro-N-phenylphthalimide, 3-fluoro-N-phenylphthalimide, and 3-chloro-N-phenylphthalimide. Various methods are known in the art for preparing 3-substituted N-phenylphthalimides, and include those methods described in F. J. Williams & P. E. Donahue, *J. Org. Chem.*, 42, 3414 (1977) and F. J. Williams & P. E. Donahue, *J. Org. Chem.*, 43, 255 (1978).

Suitable aromatic dihydroxy anions can be derived from the following dihydric phenols:
2,2-bis-(2-hydroxyphenyl)propane,
2,4'-(dihydroxyphenyl)methane,
bis-(2-hydroxyphenyl)methane,
2,2-bis-(4-hydroxyphenyl)propane hereinafter identified as bisphenol-A or BPA,
1,1-bis-(4-hydroxyphenyl)ethane,
1,1-bis-(4-hydroxyphenyl)propane,
2,2-bis-(4-hydroxyphenyl)pentane,
3,3-bis-(4-hydroxyphenyl)pentane,
4,4'-dihydroxybiphenyl,
4,4'-dihydroxy-3,3,5,5'-tetramethylbiphenyl,
2,4'-dihydroxybenzophenone,
4,4'-dihydroxydiphenylsulfone,
2,4'-dihydroxydiphenylsulfone,
4,4'-dihydroxydiphenylsulfoxide,
4,4'-dihydroxydiphenylsulfide,
hydroquinone,
resorcinol,
3,4'-dihydroxyphenylmethane,
4,4'-dihydroxybenzophenone,
2,4'-dihydroxybenzophenone and
4,4'-dihydroxydiphenylether The reaction components can be placed in a single reaction vessel, which simplifies the procedure. In carrying out the method of the present invention, at least 1.5 moles, and preferably 1.9 to 2.1 moles, of a 3-substituted N-arylphthalimide of formula II are reacted with 1 mole of an aromatic dihydroxy dianion compound of formula III. Too large a molar excess of a phthalimide may present difficulties in separating and recovering any unreacted phthalimide.

The amount of non-polar solvent used can vary widely, but a sufficient amount should be employed to effect a liquid medium for the reaction to proceed. On a weight basis, from about 1 to about 20 parts of non-polar solvent are employed per unit of weight of the total weight of the two reactants, namely the phthalimide of formula II and the aromatic dihydroxide dianion of formula III. Non-polar solvents which can be employed to practice this invention include, but are not limited to, toluene, isomeric xylenes, such as m-, o- and p-xylene, benzene, ethylbenzene, octane, cycloheptane and hexane.

The process of the present invention can be carried out over a wide range of temperatures. Generally, the reagents are refluxed at temperatures ranging from about 100° C. to about 200° C. and is completed within a range of about one to about twenty hours, depending upon the specific reactants employed as well as the temperature at which the reaction is performed.

The reaction is conducted under bisimide-forming conditions. These conditions include a substantially anhydrous reaction medium and advantageously an inert atmosphere, such as nitrogen. The reaction mixture is also preferably stirred to insure intimate contact of all the reactants and reagents required for optimum processing.

After the reaction is completed, the reaction solution is washed and purified according to conventional techniques, e.g., employing dilute sodium hydroxide solutions or precipitation of the product by addition of an anti-solvent, i.e., methanol, to remove any unreacted starting materials. The mixture is then dried, for example, with magnesium sulfate and concentrated by suitable means, such as under a vacuum, to give a solid bisimide which is essentially pure at this stage. It is believed that because no phase transfer catalyst decomposition products can be formed in this reaction, the final product of this invention is more pure than products prepared by prior art processes.

The method of the present invention for preparing an aromatic bisimide is simpler, less expensive and safer than current methods which employ a phase transfer catalyst and/or a dipolar aprotic solvent. Both phase transfer catalysts and dipolar aprotic solvents are costly and also can be difficult to recover and purify after use. Phase transfer catalysts partially decompose during a reaction to yield carcinogenic nitrosamines thus, presenting a hazard to those performing the reaction process. Dipolar aprotic solvents also are toxic and can present occupational hazards. Consequently, the method of the present invention is not only more cost efficient, but also eliminates the hazards found in methods which employ a phase transfer catalyst and/or a dipolar aprotic solvent.

The following Example 1 illustrates the feasibility of reacting a 3-substituted-N-arylphthalimide and an aromatic hydroxy anion in a non-polar solvent without the use of a phase transfer catalyst.

EXAMPLE 1

A stirred mixture of 1.238 gm (0.004620 moles) of 3-nitro-N-phenylphthalimide, 0.5720 gm (0.004400 moles) of anhydrous p-cresol sodium salt of the formula:

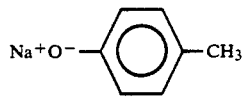

0.3616 gm (0.001570 moles) of o-terphenyl (as an internal standard), and 2.3 ml of toluene was refluxed under nitrogen for 1 hour at which time analysis by gas chromatography showed 89.8% conversion to the desired 3 cresoxy-N phenylimide product of formula

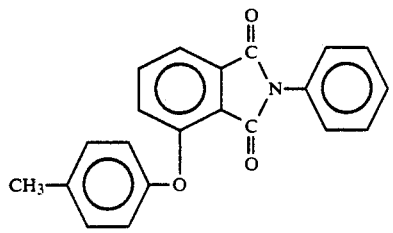

Examples 2–4 are provided to illustrate and to more particularly point out and describe the invention, that is, preparing an aromatic bisimide by effecting a reaction between a 3-sustituted N-arylphthalimide and an aromatic dihydroxide dianion in a non-polar solvent without the use of a phase transfer catalyst. These examples are merely illustrative and not intended to be limiting.

EXAMPLE 2

A stirred mixture of 12.9 gm (0.0481 moles) of 3-nitro-N-phenylphthalimide, 6.62 gm (0.0243 moles) of anhydrous disodium salt of bisphenol A (BPA), and 25 ml of tolulene was refluxed 2 hours, cooled to approximately 60° C., and diluted with 150 ml of methanol to effect precipitation of the desired product 3,3-N phenyl BPA bisimide having the formula:

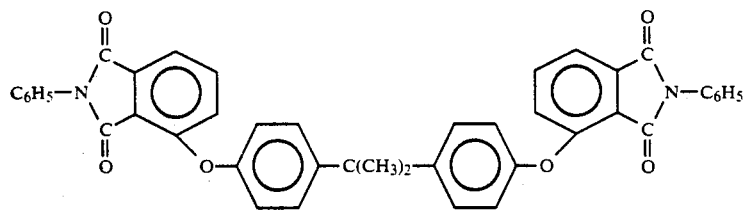

illustrated in Example 1. The solid obtained was washed with methanol and dried overnight in vacuo at 80° C. to afford 10.4 gm (65% yield) of product.

EXAMPLE 3

A mixture of 1.36 gm (0.0050 moles) of anhydrous disodium salt of BPA, 5 ml of azeotropically dried toluene, and 2.68 gm (0.00990 moles) of 3-nitro-N-phenylphthalimide was refluxed for 2.5 hours with stirring. Small (0.2 ml) aliquots were removed after 45 and 120 minutes of reflux. High pressure liquid chromatography (HPLC) analysis showed 78% conversion to 3,3-N-phenyl BPA bisimide after 45 min and 95% conversion after 120 minutes, based on 3-nitro-N-phenylphthalimide starting material.

EXAMPLE 4

A mixture of 0.75 gm (0.0028 moles) of anhydrous disodium salt of BPA, 3 ml of azeotropically dried toluene, and 1.31 gm (0.0055 moles) of 3-fluoro-N-phenylphthalimide was refluxed 3 hours with stirring. Small aliquots were removed after 60 and 120 minutes. HPLC analysis showed 15% conversion to 3,3-N-phenyl BPA bisimide after 60 minutes and 32% conversion after 120 minutes. Though slower than the nitro substituted compound used in Example 4 the fluoro substituted compound also reacts without a phase transfer catalyst.

I claim:

1. A process for preparing aromatic imides of the general formula

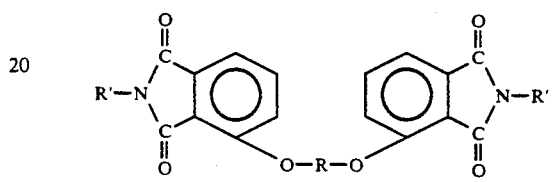

which consists of (1) reacting 3-substituted N-arylphthalimide of the general formula

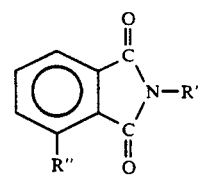

with a dianion of an aromatic dihydroxy compound of the general formula

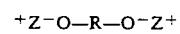

under bisimide-forming conditions, where Z is an alkali metal, R comprises (a) divalent radicals of the formula

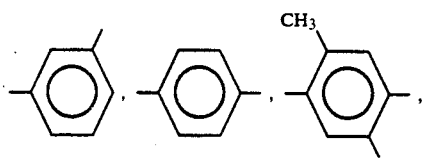

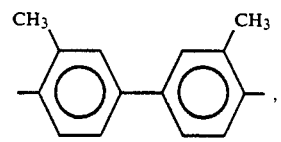

-continued

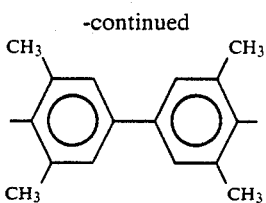

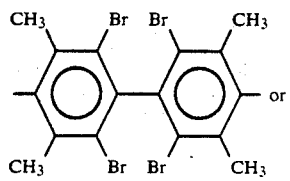 or

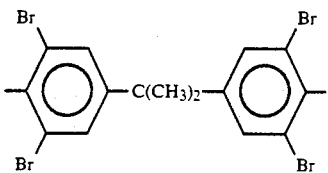

or (b) divalent organic radicals of the general formula

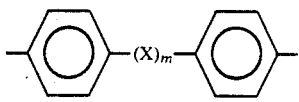

where X comprises a divalent radical of the formula —$C_yH_{2y}$—, —CO—, —$SO_2$—, —SO—, —O— or —S—, wherein m is 0 or 1, y is a whole number from 1 to 5, R' is an aryl radical having from 6 to 20 carbon atoms and R" comprises $NO_2$, CN, F, Br, or Cl the reaction being conducted in a non-polar solvent and (2) isolating the formed aromatic bisimide.

2. The process of claim 1, wherein the non-polar solvent comprises toluene, o-xylene, m-xylene, p-xylene, benzene, ethylbenzene, hexane, octane or cycloheptane.

3. The process of claim 1, wherein the 3-substituted N-arylphthalimide is 3-nitro-N-phenylphthalimide.

4. The process of claim 1, wherein the 3-substituted N-arylphthalimide is 3-fluoro-N-phenylphthalimide.

5. The process of claim 1, wherein the 3-substituted N-arylphthalimide is 3-chloro-N-phenylphthalimide.

6. The process of claim 1, wherein the aromatic dihydroxy dianion compound is from bisphenol-A.

7. The process of claim 1, wherein the aromatic dihydroxy dianion compound is from 4,4'-dihydroxydiphenyl.

8. The process of claim 1, wherein the aromatic dihydroxy dianion compound is from 4,4'-dihydroxydiphenyloxide.

9. The process of claim 1, wherein the aromatic dihydroxy dianion compound is from 4,4'-dihydroxydiphenylsulfide.

10. A method for preparing an aromatic bisimide having the following formula

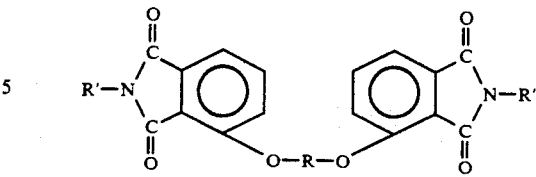

which consists of effecting a reaction under substantially anhydrous conditions between 3-nitro-N-phenylphthalimide and bisphenol-A dianion by refluxing in toluene and (2) isolating the formed aromatic bisimide, wherein R comprises (a) divalent radicals of the formula

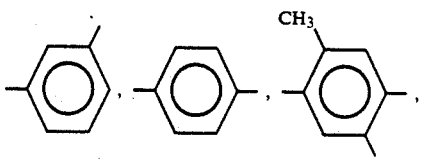

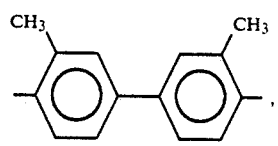

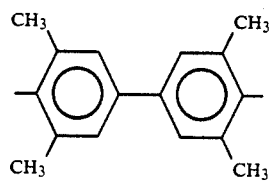

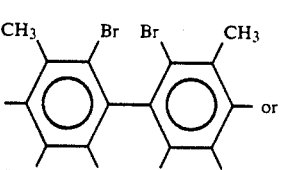 or

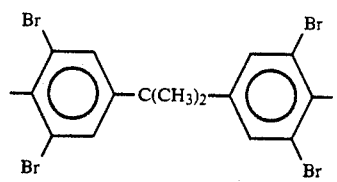

or (b) divalent organic radicals of the general formula

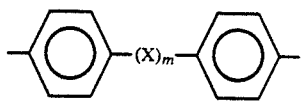

where X comprises a divalent radical of the formula —$C_yH_{2y}$—, —CO—, —$SO_2$—, —SO—, —O— or —S—, wherein m is 0 or 1, y is a whole number from 1 to 5, where R' is an aryl radical having from 6 to 20 carbon atoms.

* * * * *